US00PP27255P3

(12) United States Plant Patent
Nir

(10) Patent No.: US PP27,255 P3
(45) Date of Patent: Oct. 11, 2016

(54) ***CHAMELAUCIUM* PLANT NAMED 'JUPITER'**

(50) Latin Name: *Chamelaucium uncinatum*
Varietal Denomination: JUPITER

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 114 days.

(21) Appl. No.: 14/544,374

(22) Filed: Dec. 30, 2014

(65) Prior Publication Data

US 2016/0192559 P1 Jun. 30, 2016

(51) Int. Cl.
*A01H 5/02* (2006.01)

(52) U.S. Cl.
USPC ..... Plt./229

(58) Field of Classification Search
USPC ..... Plt./229
See application file for complete search history.

*Primary Examiner* — Anne Grunberg
(74) *Attorney, Agent, or Firm* — Cassandra Bright

(57) ABSTRACT

A new and distinct *Chamelaucium* cultivar named 'JUPITER' is disclosed, characterized by a large quantity of very early blooming, medium sized, red-purple colored flowers. Flowers uniquely occur in both terminal and axillary positions. The new variety is a *Chamelaucium*, normally producing cut flower stems, or as a garden or container plant.

1 Drawing Sheet

Latin name of the genus and species: *Chamelaucium uncinatum.*

Variety denomination: 'JUPITER'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a hybrid seedling from the breeding program at a commercial nursery in Kfar Hess, Israel.

The crossing resulting in this new variety was made during 2008. The seed parent is the variety referred to as *Chamelaucium uncinatum* 'Rotemwax,' U.S. Plant Pat. No. 26,024. The pollen parent is the unpatented, variety referred to as *Chamelaucium uncinatum* 'Early Violet'. The new variety was discovered in August of 2010 by the inventor in a group of seedlings resulting from previously mentioned crossing, in a commercial nursery in Kfar Hess, Israel.

Asexual reproduction of the new cultivar has been performed by vegetative cuttings. This was first performed at a commercial nursery in Kfar Hess, Israel in April of 2011 and has shown that the unique features of this cultivar are stable and reproduced true to type in successive generations.

SUMMARY OF THE INVENTION

The cultivar 'JUPITER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JUPITER'. These characteristics in combination distinguish 'JUPITER' as a new and distinct *Chamelaucium* cultivar:

1. Very early blooming season.
2. Unique red-purple colored flower and red flower bud.
3. Medium flower size.
4. Both terminal and axillary flowers, forming a dense spray of abundant flowers.

PARENT COMPARISON

Plants of the new cultivar 'JUPITER' are similar to plants of the seed parent, *Chamelaucium uncinatum* 'Rotemwax' in most horticultural characteristics, however, plants of the new cultivar 'JUPITER' bloom earlier, and produce flowers in both terminal and axillary positions, compared to only terminal occurring flowers of the seed parent. 'JUPITER' also produces slightly less flowering stems per year than the seed parent.

Plants of the new cultivar 'JUPITER' are similar to plants of the pollen parent; *Chamelaucium uncinatum* 'Early Violet' in most horticultural characteristics, however, plants of the new cultivar 'JUPITER' bloom earlier, and produce flowers in both terminal and axillary positions, compared to only terminal occurring flowers of the pollen parent. Additionally, plants of 'JUPITER' produce larger flowers of a lighter red-purple color than the pollen parent.

COMMERCIAL COMPARISON

Plants of the new cultivar 'JUPITER' are comparable to the variety *Chamelaucium uncinatum* 'M.B. Violet', unpatented. The two *Chamelaucium* varieties are similar in most horticultural characteristics; however, the new variety 'JUPITER' differs in the following:

1. Flowers produced during September through November, whereas this comparator produces flowers during February through March.
2. Flowers are darker red-purple than those of 'M.B. Violet.'
3. Flowers are produced in both terminal and axillary positions, compared to only terminal occurring flowers of this comparator.

Plants of the new cultivar 'JUPITER' can also be compared to the commercial variety *Chamelaucium uncinatum* 'Nir Eden,' U.S. Plant Pat. No. 26,214. These varieties are similar in most horticultural characteristics however, the new variety 'JUPITER' differs in the following:

1. Flowers produced during September through November, whereas this comparator produces flowers during February through March.
2. Flowers are smaller, on average 1.5 cm, compared to 2.0 cm diameter flowers from plants of 'Nir Eden.'
3. Flowers are produced in both terminal and axillary positions, compared to only terminal occurring flowers of this comparator.

BRIEF DESCRIPTION OF THE PHOTOGRAPH

The accompanying photograph in FIG. 1 illustrates in full color a close up of typical flowers and foliage of 'JUPITER' at approximately 1 year of age.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'JUPITER' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'JUPITER'.

Age of plant described: At least 2 months old from a rooted cutting.

Typical flowering stems harvested per plant: 100 during the course of the season.

Vase life of flowers: Two weeks.

PROPAGATION

Time to produce a rooted plantlet: 30 to 60 days at approximately 24° C.

Root description: Fibrous.

PLANT

Growth habit: Upright plant produces multiple stems from a pinch, or after harvesting stems.

Height: 150 cm.

Plant spread: 50 cm.

Growth rate: Rapid.

Branching characteristics: Moderate branching occurs after pinching.

Length of primary lateral branches: 60 cm to 90 cm on average.

Diameter of lateral branches: 0.2-0.3 cm.

Quantity of primary lateral branches: 80 to 100, these are the harvested flowering stems.

Characteristics of primary lateral branches:

*Form.*—Round.

*Diameter.*—0.5 to 0.6 cm.

*Color.*—Near RHS Grey-Grown 199A.

*Texture.*—Smooth.

*Strength.*—Stems somewhat brittle.

Internode length: Range from 2.0 to 8.0 cm.

FOLIAGE

Leaf:

*Arrangement.*—Opposite.

*Quantity.*—Approximately 6 leaves, in the 10-15 cm section from the top of the branch.

*Average length.*—2.0 cm.

*Average width.*—0.1 cm.

*Shape of blade.*—Needle.

*Apex.*—Acute.

*Base.*—Attenuate.

*Margin.*—Entire.

*Texture.*—Glabrous all surfaces.

*Pubescence.*—None.

*Aspect.*—Straight, occurring at approximately a 15 to 30 degree angle.

*Color.*—Young foliage: Near RHS Green 137A. Mature foliage: Near RHS Green 137A.

*Venation.*—Indistinguishable from foliage.

*Petiole.*—Not present.

FLOWER

Natural flowering season: Plants planted during April through October begin flowering September through November, without a juvenility period in Kfar Hess, Israel. Plants flower continuously under short day conditions.

Days to flowering from rooted cutting: Approximately 60 days.

Inflorescence type: Terminal Panicle.

Individual flower type: Single, rotate 5 petaled with a cone shaped hypanthium. Flowers outwardly facing.

Persistent or self-cleaning: Self-Cleaning.

Lastingness: About 10 days in a vase. Approximately 45 to 60 days on the plant.

Typical flowering stem length: Approximately 60 to 80 cm.

Bud:

*Shape.*—Spherical.

*Length.*—0.3 cm.

*Diameter.*—0.3 cm.

*Color.*—Near RHS Red 47A.

Inflorescence size:

*Diameter.*—Average 28 cm.

*Length.*—Average 35 cm.

Flower size:

*Diameter.*—Average 1.5 cm.

*Length.*—Average 0.7 cm.

Corolla:

*Petals.*—Arrangement: Rotate, not overlapping. Length: Average 0.4 cm. Diameter: Average 0.5 cm. Quantity: 5. Texture: Smooth. Apex: Obtuse rounded. Base: Fused into a hypanthium.

*Color.*—When opening: Upper surface: Near RHS Red-Purple 72B. Lower surface: Near RHS Red-Purple 72B. Fully opened: Upper surface: Near RHS Purple N79C. Lower surface: Near RHS Purple N79C. Aging: Upper surface: Near RHS Purple N79C. Lower surface: Near RHS Purple N79C.

*Interior corolla/tube*.—Diameter: 0.7 cm. Length: 0.4 cm.

*Color*.—When opening: Upper surface: Near RHS Grey-Brown 199A. Lower surface: Near RHS Grey-Brown 199A. Fully opened: Upper surface: Near RHS Greyed-Purple 187A. Lower surface: Near RHS Greyed-Purple 187A. Aging: Upper surface: Near RHS Purple N77A. Lower surface: Near RHS Purple N77A.

Hypanthium:

*Diameter*.—Average 0.5 cm.

*Length*.—Average 0.2 cm.

*Shape*.—Obconical.

*Color*.—When opening: Inner surface: Near RHS Grey-Brown 199A. Outer surface: Near RHS Grey-Brown 199A, flushed Greyed-Purple N186B. Fully opened: Inner surface: Near RHS Greyed-Purple N186C. Outer surface: Near RHS Greyed-Purple N186C. Aging: Inner surface: Near RHS Greyed-Purple N186A. Outer surface: Near RHS Greyed-Purple N186A.

Calyx/sepals:

*Quantity per flower*.—Fused into a single, conical structure.

*Length*.—0.2 cm.

*Width*.—0.6 cm.

*Margin*.—Entire, incised approximately 1 mm.

*Texture*.—Smooth.

*Color*.—Near RHS Green 137A, heavily flushed Greyed-Purple 187A and N186A.

Peduncle: Peduncle consists of the plant stem.

Pedicel:

*Length*.—1.2 to 2.0 cm.

*Diameter*.—0.1 cm.

*Color*.—Near RHS Yellow-Green 144A.

Fragrance: None.

REPRODUCTIVE ORGANS

Stamens:

*Number*.—10.

*Filament length*.—1 mm.

*Filament color*.—Near RHS Yellow-Orange 15D.

Anthers:

*Shape*.—Oval.

*Length*.—0.25-0.5 mm.

*Width*.—0.2 mm.

*Color*.—Near RHS Red-Purple 65D.

Pollen:

*Color*.—Near RHS Yellow-Orange 20B.

*Quantity*.—Scant to moderate.

Pistil:

*Number*.—1.

*Length*.—0.6 cm.

*Color*.—Near RHS White 155A.

*Style color*.—Near RHS White 155A.

*Stigma*.—Shape: Round. Color: Near RHS Brown 200A. Texture: Glabrous.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1.5 mm, brown in color, too minute to accurately measure color with R.H.S. chart.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named 'JUPITER' as herein illustrated and described.

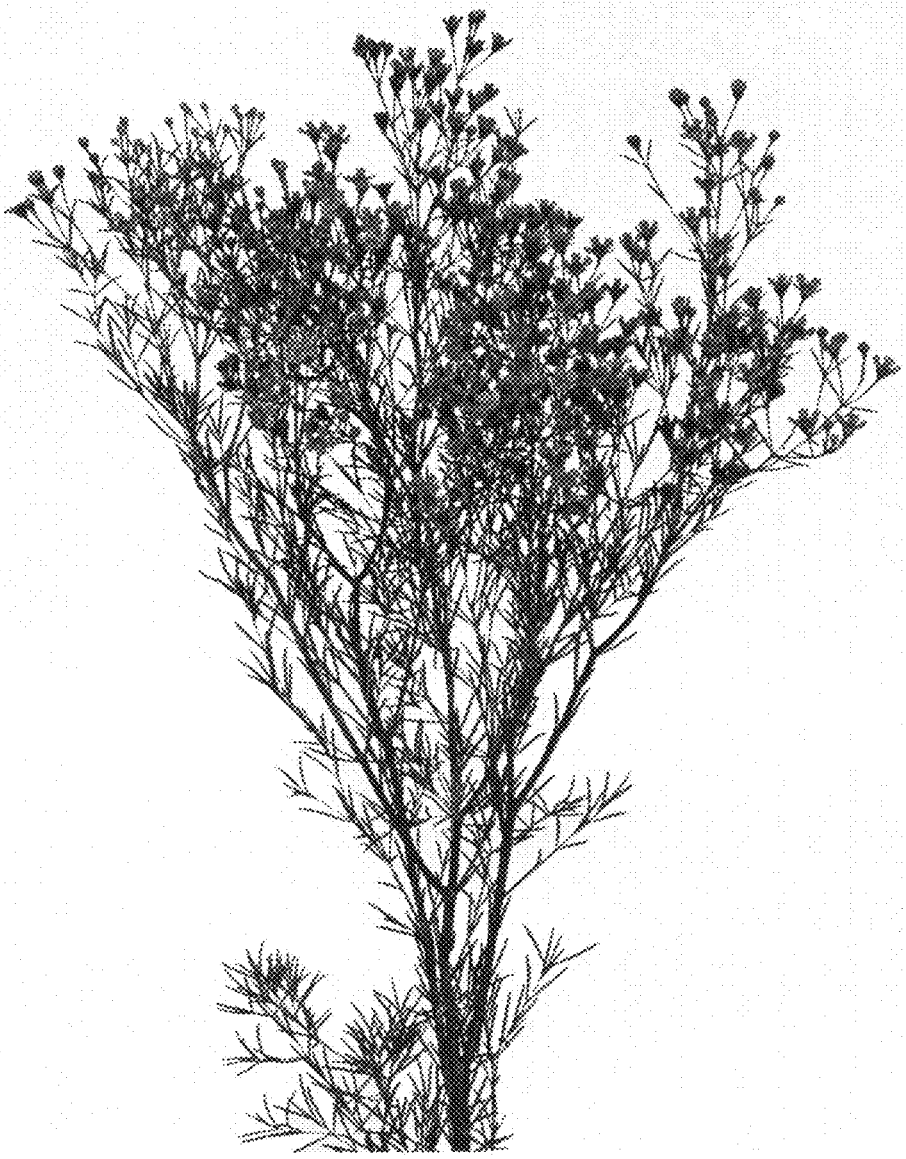

* * * * *